United States Patent
Gulledge

[19]

[11] Patent Number: 6,080,122
[45] Date of Patent: Jun. 27, 2000

[54] MOTION RESTRAINING BRACE

[76] Inventor: Ronald E. Gulledge, 621 Willow Run, Lakeland, Fla. 33813

[21] Appl. No.: 09/138,936

[22] Filed: Aug. 24, 1998

[51] Int. Cl.$^7$ ........................................................ A61F 5/00
[52] U.S. Cl. ................................... 602/16; 602/5; 602/20
[58] Field of Search .................................. 602/5, 16, 20, 602/21, 22, 26, 27; 482/127, 129; 403/52, 83, 109.3, 109.8, 112, 113, 119

[56] References Cited

U.S. PATENT DOCUMENTS

| | | | |
|---|---|---|---|
| 4,817,588 | 4/1989 | Bledsoe | 602/16 |
| 5,460,599 | 10/1995 | Davis et al. | 602/16 X |

*Primary Examiner*—Kim M. Lee
*Attorney, Agent, or Firm*—William M. Hobby, III

[57] ABSTRACT

A motion restraining brace apparatus for attachment to a patient's joint, such as across the knees or the elbows, to restrain the angle of motion of a brace. A base plate has a locking gear member rotatably attached thereto and having a plurality of locking notches along the edge thereof. A first restraining bar is rotatably attached to the gear and extends therefrom and a second restraining bar is fixedly attached to the gear and extends therefrom. A locking gear member has a locking pin movably attached to the base plate and positioned to move in and out of one gear member notch to lock the gear member to the base plate at a predetermined position to prevent rotation of the gear member relative to the base plate. A stop pin is attached to the base plate to stop the rotation of the first restraining bar in one direction of rotation while the stop surface in one end of the first and second restraining bars are positioned to abut each other to stop the rotation of one of the restraining bars in a second direction of rotation. A cover plate is also attached to a base plate over the gear member and has degree markings thereon to allow the rapid positioning of the locking pin for a predetermined degree of rotation of the first and second restraining bars.

12 Claims, 2 Drawing Sheets

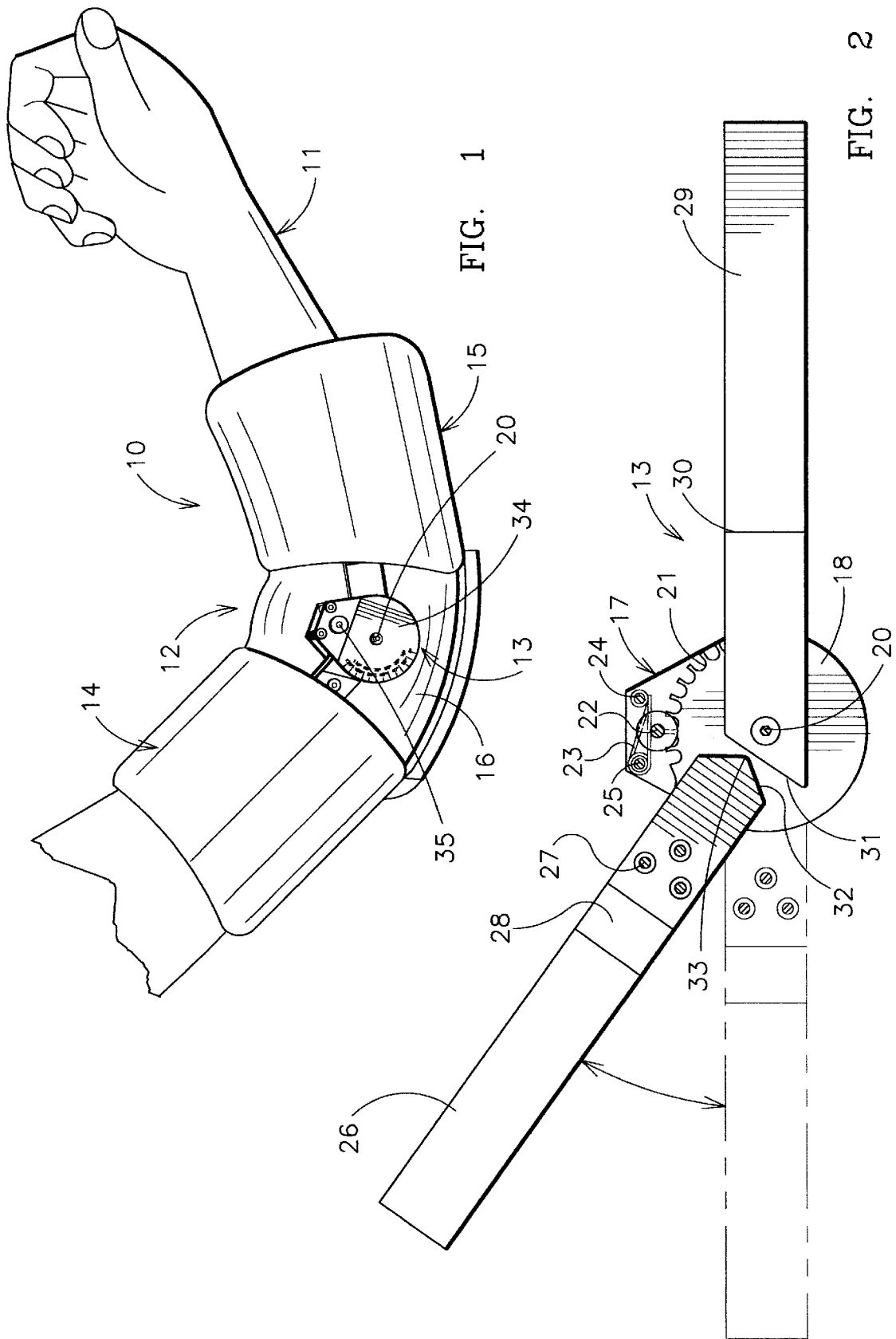

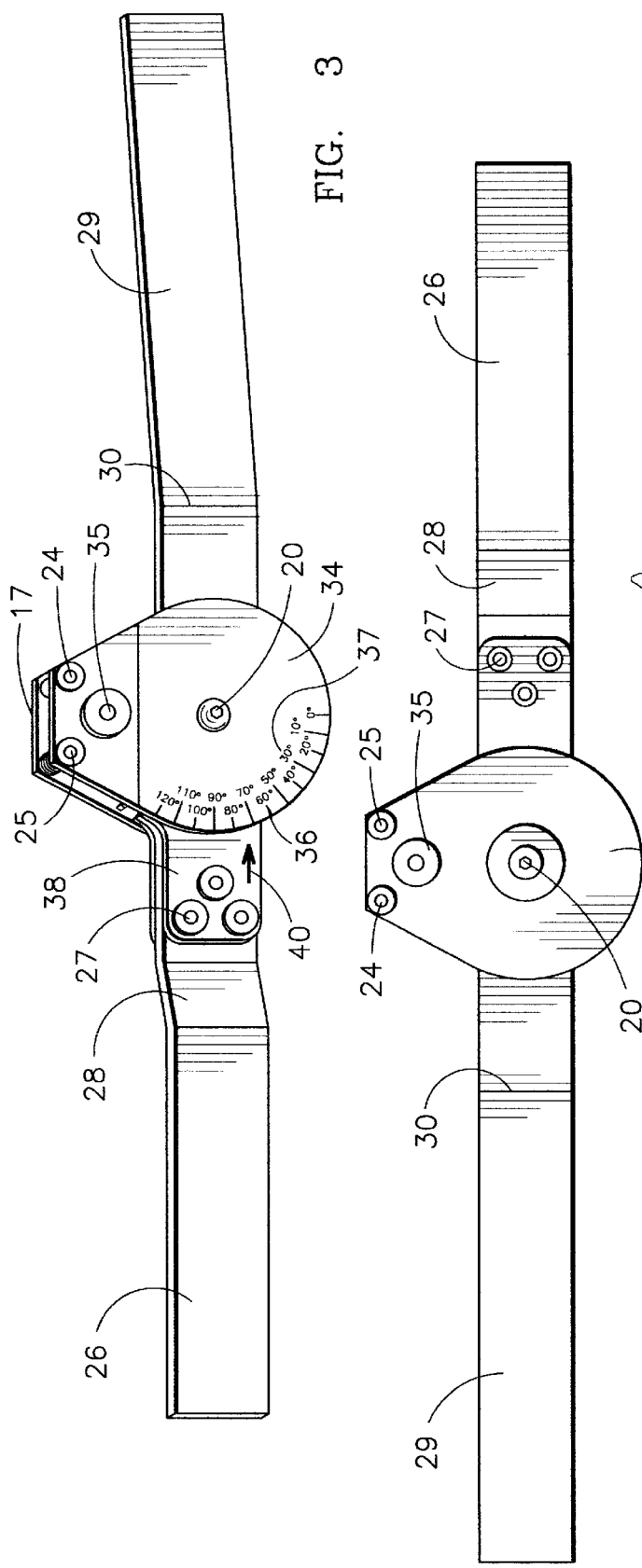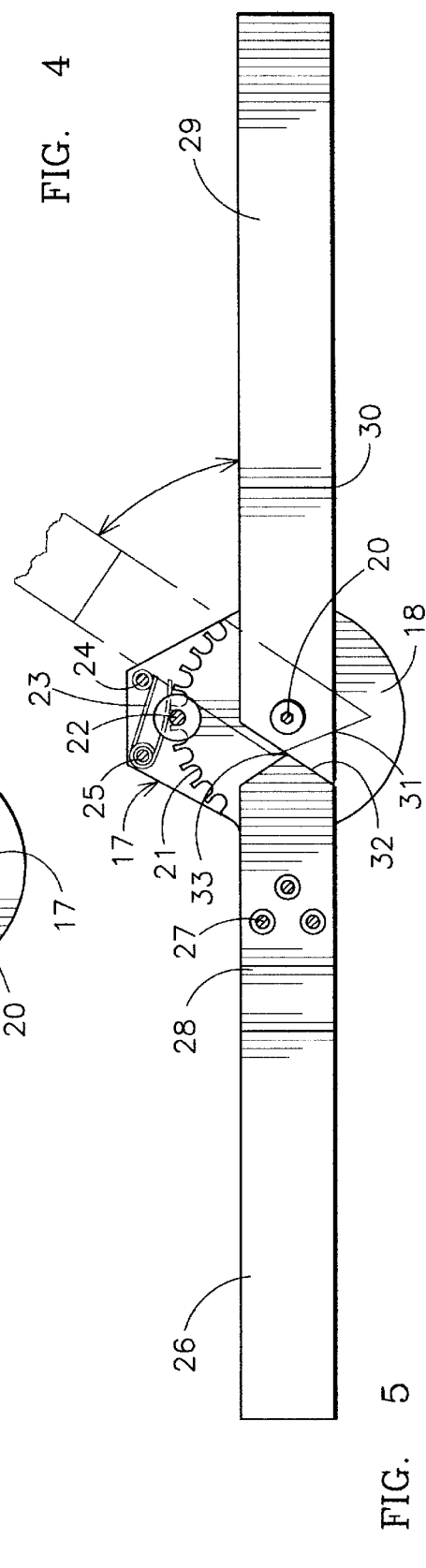

MOTION RESTRAINING BRACE

BACKGROUND OF THE INVENTION

The present invention relates generally to orthopedic appliances and more particularly to a motion restraining brace for restricting the pivotal motion of a patient's joint.

Joint injuries, including injuries to the knee and elbow, and knee and elbow surgery, often make it necessary to restrict pivotal motion of the joint to a predetermined angular range while the joint heals. This pivotal restraint is typically accomplished by a joint motion restraining brace having a pair of articulated side portions positionable on opposite lateral sides of the leg. Each of these side portions is conventionally defined by elongated support members which are pivotally connected at one end by an adjustable hinge mechanism which is positionable on one side of the joint. The restraining arms of such a brace are secured to their associated arm or leg portion by straps and cushion pad members which encircle the leg or arm and may be adjustably tightened or loosened against the leg or arm to hold the support members firmly in place. The hinge mechanisms are typically adjustable to selectively limit the relative pivotal motion between the interconnected support members on opposite sides of the leg to thereby limit the pivotal motion of the human joint to a predetermined angular range. Thus, it may be medically necessary to restrict the movement of the joint to a pivotal range extending between a 30 degree and a 90 degree angle. The hinge mechanisms can be adjusted to limit the relative pivotal motion of each of the interconnected support members to this range.

It has been common to use pairs of conventional knee braces of this general type which have proven to be beneficial in protecting knee joints following an injury thereto or surgery thereon. These knee braces have typically had a variety of problems resulting from the complexity of the adjustable hinge for the brace. The present invention is directed towards a single angle restricting joint brace which can be easily and rapidly adjusted for varying the pivotal angle that the joint can be rotated. The angle can be adjusted as desired during the healing period or for different patients. One of the problems with prior braces is the interconnecting hinge of each of a pair of support members which has been somewhat awkward and laborous to adjust and has been prone to undesirable slippage.

One prior art Bledsoe, U.S. Pat. No. 4,817,588, teaches a motion restraining knee brace having a pair of articulated side portions each defined by elongated thigh and calf support members pivotally interconnected by an adjustable hinge mechanism. Each hinge mechanism has a single adjustment dial that cooperates with a pair of stop members to selectively limit the relative pivotal movement between the thigh and calf support members associated with the hinge. The support members are securable to the leg by connecting straps which encircle the leg and have independently adjustable anterior and posterior portions. This motion restraining knee brace is, however, somewhat complex for use in many elbow and knee injuries and following many types of joint surgery.

The present invention simplifies the motion restraining brace especially for use on the elbow and knee following joint injuries or surgery.

SUMMARY OF THE INVENTION

A motion restraining brace apparatus attaches to a patient's joint, such as across the knees or elbows, to restrain the angle of motion of the brace. A base plate has a locking gear member rotatably attached thereto having a plurality of locking notches along the edge thereof. A first restraining bar is rotatably attached to the gear and extends therefrom and a second restraining bar is fixedly attached to the gear and extends therefrom. A locking gear member has a locking pin movably attached to the base plate and positioned to move in and out of one gear member notch to lock the gear member to the base plate at a predetermined position to prevent rotation of the gear member relative to the base plate. A stop pin is attached to the base plate to stop the rotation of the first restraining bar in one direction of rotation while the stop surface in one end of the first and second restraining bars are positioned to abut each other to stop the rotation of one of the restraining bars in a second direction of rotation. A cover plate is also attached to a base plate over the gear member and has degree markings thereon to allow the rapid positioning of the locking pin for a predetermined degree of rotation of the first and second restraining bars.

BRIEF DESCRIPTION OF THE DRAWINGS

Other objects, features, and advantages of the present invention will be apparent from the written description and the drawings in which:

FIG. 1 is a perspective view of a restraining brace in accordance with the present invention attached to a patient's arm;

FIG. 2 is a side elevation of the restraining brace restraining mechanism;

FIG. 3 is a perspective view of the restraining mechanism of FIG. 2;

FIG. 4 is a rear side elevation of the restraining brace mechanism of FIG. 3; and FIG. 5 is a side elevation of the restraining brace mechanism of FIGS. 1–4 having the cover removed.

DESCRIPTION OF THE PREFERRED EMBODIMENT

Referring to FIGS. 1–5 of the drawings, a motion restraining brace 10 is shown attached to a patient's arm 11 over the elbow area 12 of the arm. The motion restraining brace 10 has a motion restraining mechanism 13 having limb attaching pads 14 and 15 attached thereto along with a joint covering pad 16. The motion restraining mechanism has a base plate arm 17 having a gear member 18 rotatable attached with a center pin 20. The gear member 18 has a plurality of notches 21 along one edge thereof for receiving a locking pin 22 which can slide into any one of the notches 21 to lock the rotatable mounted gear member 18 to the base plate 17 at a plurality of desired positions of rotation. The locking pin 22 has a spring 23 mounted between a first stop pin 24 and a second stop pin 25 attached to the base plate 17. The spring 23 is attached around the second stop pin 25 as seen in FIG. 2. A first restraining bar 29 is rotatable attached on the pin 20 to the base plate 17 while a second restraining bar 26 is fixedly attached to the rotatable gear member 21 with a plurality of attaching fasteners 27. The bar 26 can be riveted or welded or formed as one piece with gear member 18. Bar 26 can have a positioning bend 28 therein while the bar 29 can have a positioning bend 30 therein. The first restraining bar 29 has an angled stop edge 31 while the second restraining bar 26 has an angled stop edge 32 on one end thereof and, as illustrated, has a pointed end 33 forming two angled edges.

The cover plate 34, as illustrated in FIG. 3, covers the mechanism, as illustrated in FIGS. 2 and 4, and is held to the base plate 17 with the stop members 24 and 25. A handle portion 35 of the stop pin 22 is on the outside of the cover plate 34 where it can be easily grasped and lifted against the spring 23 for raising the stop pin 22 out of one of the notches 21 of the rotatable gear portion 18. This allows the gear portion to be rotated to a desired angle where the stop pin 20 can be released into notch 21. The cover plate 34 also has the pin 20 extending therethrough and has a plurality of degree markings 36 on the face thereof along with indicia 37. The second restraining bar 26 on the gear 18 on extension 38 has an index pointer 40 thereon for aligning the degree markings 36 therewith when adjusting the angle of rotation of the motion restraining mechanism 13.

In operation, the motion restraining mechanism can be adjusted by raising the handle 35 of the stop pin 22, rotating the bracing arm 26 and gear member 18 to align the pointer 40 with the degree markings 36 for a predetermined angle setting and then releasing the handle 35 to allow the stop pin 22 to engage a notch 21 on the gear member 18 to lock it in place and locked to the base 17. The second bracing arm 29 can then be rotated in one direction until it abuts with the stop pin 24, as illustrated in FIG. 5, and can be rotated in the opposite direction until angled the stop surface 31 engages angled the stop surface 32 of the motion restraining bar 26. The motion restraining bar 29 thus rotates between the stop pin 24 on the base 17 in one direction and with the abutment of the stop surfaces 31 and 32 in the opposite direction. The abutment is adjustable by rotating the gear member 18 to any desired position. The gear member 18 in the fixedly attached restraining arm 26 are shown locked in one position in FIG. 2 and in another position in FIG. 5. The locking mechanism 13 is easily attached to a person's joints using conventional attachment pads 14 and 15.

It should be clear at this time that an adjustable swivel brace has been provided for the treatment of flexion characteristics and may be adjusted in 10 degree increments or in any degree increments as desired which can be readily adjusted by the sliding of a spring loaded pin in and out of notches within a rotatable gear member. However, the present invention is not to be limited to the forms shown which are to be considered illustrative rather than restrictive.

I claim:

1. A motion restraining brace apparatus comprising:
   a base plate;
   a locking gear member rotatably attached to said base plate and having a plurality of locking notches along one edge thereof;
   a first restraining bar rotatably attached to said gear member and having two end portions, one end portion extending from one side of said gear member and a second end portion having a stop edge thereon;
   a second restraining bar fixedly attached to said gear member and extending from one side thereof;
   a locking pin movably attached to said base plate and positioned to move into and out of one the gear member notches to lock said gear member and second restraining bar to said base member to prevent rotation of said gear member and second restraint bar relative to said base plate;
   a stop pin attached to said base plate for stopping the rotation of said first restraining bar in one direction of rotation; and
   stop means fixedly attached to said gear member to stop said first restraining bar in a second direction of rotation, wherein the motion restraining joint brace has a pair of restraining bars hinged together to allow rotation of the restraining bars relative to each other by a set degree of rotation.

2. The motion restraining brace apparatus in accordance with claim 1 having attaching means for attaching said first and second restraining bars to a person's limbs over a joint.

3. The motion restraining brace apparatus in accordance with claim 2 in which said second restraining bar has a stop surface formed thereon for engaging said first restraining bar stop edge.

4. The motion restraining brace apparatus in accordance with claim 3 in which said first restraining bar has an angled end stop edge on one end thereof.

5. The motion restraining brace apparatus in accordance with claim 4 in which said second restraining bar has generally pointed end for engaging said first restraining bar angled stop edge.

6. The motion restraining brace apparatus in accordance with claim 5 including a cover plate attached to said base plate over said gear member.

7. The motion restraining brace apparatus in accordance with claim 6 in which said cover plate has degree markings thereon.

8. The motion restraining brace apparatus in accordance with claim 7 in which said second restraining bar has a mark thereon for aligning the first restraining bar with said cover plate degree markings.

9. The motion restraining brace apparatus in accordance with claim 8 in which said attaching means includes a pair of arm pads attached to said first and second restraining bars.

10. The motion restraining brace apparatus in accordance with claim 9 in which said locking pin has a spring attached thereto for biasing said locking pin into one of said gear member locking notch.

11. The motion restraining brace apparatus in accordance with claim 10 in which said spring is mounted to said stop pin.

12. The motion restraining brace apparatus in accordance with claim 11 including a second stop pin holding said cover plate to said base plate and having said spring attached thereon.

* * * * *